United States Patent
Park

(10) Patent No.: US 11,406,589 B2
(45) Date of Patent: Aug. 9, 2022

(54) CUTIBACTERIUM GRANULOSUM STRAIN, AND COMPOSITION COMPRISING SUCH STRAIN OR CULTURE THEREOF FOR PREVENTING OR TREATING ACNE

(71) Applicant: GENOME AND COMPANY, Gyeonggi-do (KR)

(72) Inventor: Han-Soo Park, Seoul (KR)

(73) Assignee: GENOME AND COMPANY, Gyeonggi-do (KR)

(*) Notice: Subject to any disclaimer, the term of this patent is extended or adjusted under 35 U.S.C. 154(b) by 0 days.

(21) Appl. No.: 17/270,494

(22) PCT Filed: May 24, 2019

(86) PCT No.: PCT/KR2019/006241
§ 371 (c)(1),
(2) Date: Feb. 23, 2021

(87) PCT Pub. No.: WO2020/040408
PCT Pub. Date: Feb. 27, 2020

(65) Prior Publication Data
US 2021/0315801 A1    Oct. 14, 2021

(30) Foreign Application Priority Data
Aug. 23, 2018  (KR) .................. 10-2018-0098880

(51) Int. Cl.
| | |
|---|---|
| *A01N 63/00* | (2020.01) |
| *A61K 8/99* | (2017.01) |
| *A61P 17/10* | (2006.01) |
| *A61K 35/741* | (2015.01) |
| *A61Q 19/00* | (2006.01) |
| *C12N 1/20* | (2006.01) |

(52) U.S. Cl.
CPC .............. *A61K 8/99* (2013.01); *A61K 35/741* (2013.01); *A61P 17/10* (2018.01); *A61Q 19/00* (2013.01); *C12N 1/20* (2013.01)

(58) Field of Classification Search
CPC ........................................................ A61K 8/99
See application file for complete search history.

(56) References Cited

U.S. PATENT DOCUMENTS 4,548,942 A    10/1985   Shroot et al.

FOREIGN PATENT DOCUMENTS

| CN | 106661543 A | 5/2017 |
| JP | H09-20638 A | 1/1997 |
| KR | 10-1927988 B1 | 12/2018 |
| WO | WO-2015/195845 A1 | 12/2015 |
| WO | WO-2016/009377 A1 | 1/2016 |
| WO | WO-2017/184992 A1 | 10/2017 |

OTHER PUBLICATIONS

International Search Report from corresponding PCT Application No. PCT/KR2019/006241, dated Sep. 10, 2019.
Corvec, S., "Clinical and Biological Features of *Cutibacterium* (Formerly *Propionibacterium*) *avidum*, an Underrecognized Microorganism", Clinical Microbiology Reviews, Jul. 2018, vol. 31, Issue 3, pp. 1-42.
Eady, E. A., et al.; "Inhibitors produced by propionibacteria and their possible roles in the ecology of skin bacteria", Proceedings of the Royal Society of Edinburgh, 79N, 193-199, 1980.
Fujimura, S., et al.; "Purification and Properties of a Bacteriocin-Like Substance (Acnecin) of Oral *Propionibacterium acnes*", Antimicrobial Agents and Chemotherapy, Dec. 1978, p. 893-898, vol. 14, No. 6.
Shehadeh, N. H., et al.; "The Bacteriology of Acne", Arch Dermatol. 1963; 88(6):829-831.
Scholz, C. F. P., et al.; "The natural history of cutaneous propionibacteria, and reclassification of selected species within the genus *Propionibacterium* to the proposed novel genera *Acidipropionibacterium* gen. nov., *Cutibacterium* gen. nov. and *Pseudopropionibacterium* gen. nov.", International Journal of Systematic and Evolutionary Microbiology (2016), 66, 4422-4432.
Ko, H. L., "Propionicins, bacteriocins produced by Propionibacterium avidum", Zentralbl Bakteriol Orig. A., Sep. 241, 1978 (3), 325-8.
Spergel, J. M., et al.; "Atopic dermatitis and the atopic march", J Allergy Clin Immunol, vol. 112, No. 6, pp. S118-S127, 2003.
Bernard, P., et al.; "Antibiotic susceptibility of *Staphylococcus aureus* strains responsible for cutaneous infections in the community", 2008, 135, pp. 13-19.
Shuichi Higaki et al., "Minocycline Effectively Reduces Acid Producted by Propionibacterium granulosum", The Journal of Dermatology, 2002, vol. 29, pp. 20-22.

*Primary Examiner* — Albert M Navarro
(74) *Attorney, Agent, or Firm* — Harness, Dickey & Pierce, P.L.C.

(57) ABSTRACT

The present invention relates to *Cutibacterium granulosum* GENSC02 strain (KCTC 13597BP). The present invention also relates to a composition comprising the strain or its culture, and use thereof. The present invention is effective in improvement, prevention or treatment of acne, atopic dermatitis or skin inflammation by fine dust.

4 Claims, 17 Drawing Sheets

Specification includes a Sequence Listing.

```
gacgaacgct ggcggcgtgc ttaacacatg caagtcgtac ggtaaggccc tttcggggt      60
acacgagtgg cgaacgggtg agtaacacgt gagtaacctg cccacaactt tgggataacg    120
ctaggaaact ggtgctaata ctggatatgt gctcctgctg catggtgggg gttggaaagc    180
tccggcggtt gtggatggac tcgcggccta tcagcttgtt ggtggggtag tggcctacca    240
aggcggcgac gggtagccgg cctgagaggg tgaccggcca cattgggact gagatacggc    300
ccagactcct acgggaggca gcagtgggga atattgcaca atgggcgcaa gcctgatgca    360
gcaacgccgc gtgcgggatg acggccttcg ggttgtaaac cgctttcagc agggacgaag    420
cttttgtga cggtacctgc agaagaagca ccggctaact acgtgccagc agccgcggtg    480
atacgtaggg tgcgagcgtt gtccggattt attgggcgta aaggctcgt aggcggttga    540
tcgcgtcgga agtggaaact tgatgcttaa cgttgagcgt gctttcgata cggttgact    600
tgaagaaggt aggggaggaat ggaattcctg gtggagcggt ggaatgcgca gatatcagga    660
ggaacaccag tggcgaaggc ggttctctgg acctttcctg acgctgagga gcgaaagcgt    720
ggggagcgaa caggcttaga tacctggta gtccacgctg taaacggtgg gtactaggtg    780
tggggtccat tccacggatt ctgtaccgta gctaacgcat taagtacccc gcctggggag    840
tacggccgca aggctaaaac tcaaaggaat tgacggggcc ccgcacaagc ggcggagcat    900
gcggattaat tcgatgcaac gcgaagaacc ttacctgggt ttgacatgga tcgggagctt    960
ccagagatgg ttgtgcctct tttggggtcg gttcacaggt ggtgcatggc tgtcgtcagc   1020
tcgtgtcgtg agatgttggg ttaagtcccg caacgagcgc aacccctcgtc cactgttgcc   1080
agcaattcgg ttgggactc agtggagacc gccggggtca actcggagga aggtggggat   1140
gacgtcaagt catcatgccc cttatgtcca gggcttcacg catgctacaa tggccggtac   1200
agtgagttgc gacatcgtaa ggtggagcga atctcaaaaa gccggtctca gttcggattg   1260
gggtctgcaa ctcgacctca tgaagtcgga gtcgctagta atcgcagatc agcaacgctg   1320
cggtgaatac gttcccgggg cttgtacaca ccgcccgtca agtcatgaaa gtcggtaaca   1380
ctcgaagccg gtggcctaac acttttgtg ggggagctgt cgaaggtggg actggtgatt   1440
aggactaagt cgtaacaa                                                 1458
```

FIG. 1

SEQUENCE LISTING

```
<160> NUMBER OF SEQ ID NOS: 1

<210> SEQ ID NO 1
<211> LENGTH: 1458
<212> TYPE: DNA
<213> ORGANISM: Unknown
<220> FEATURE:
<223> OTHER INFORMATION: 16s rRNA of Cutibacterium granulosum GENSCO2

<400> SEQUENCE: 1
gacgaacgct ggcggcgtgc ttaacacatg caagtcgtac ggtaaggccc tttcgggggt      60
acacgagtgg cgaacgggtg agtaacacgt gagtaacctg cccacaactt tgggataacg     120
ctaggaaact ggtgctaata ctggatatgt gctcctgctg catggtgggg gttggaaagc     180
tccggcggtt gtggatggac tcgcggccta tcagcttgtt ggtggggtag tggcctacca     240
aggcggcgac gggtagccgg cctgagaggg tgaccggcca cattgggact gagatacggc     300
ccagactcct acgggaggca gcagtgggga atattgcaca atgggcgcaa gcctgatgca     360
gcaacgccgc gtgcgggatg acggccttcg ggttgtaaac cgctttcagc agggacgaag     420 cttttttgtga cggtacctgc agaagaagca ccggctaact acgtgccagc agccgcggtg     480
atacgtaggg tgcgagcgtt gtccggattt attgggcgta aagggctcgt aggcggttga     540
tcgcgtcgga agtggaaact tgatgcttaa cgttgagcgt gctttcgata cgggttgact     600
tgaggaaggt aggggagaat ggaattcctg gtggagcggt ggaatgcgca gatatcagga     660
ggaacaccag tggcgaaggc ggttctctgg acctttcctg acgctgagga gcgaaagcgt     720
ggggagcgaa caggcttaga taccctggta gtccacgctg taaacggtgg gtactaggtg     780
tggggtccat tccacggatt ctgtgccgta gctaacgcat taagtacccc gcctggggag     840
tacggccgca aggctaaaac tcaaaggaat tgacggggcc ccgcacaagc ggcggagcat     900
gcggattaat tcgatgcaac gcgaagaacc ttacctgggt ttgacatgga tcgggagctt     960
ccagagatgg ttgtgcctct tttggggtcg gttcacaggt ggtgcatggc tgtcgtcagc    1020
tcgtgtcgtg agatgttggg ttaagtcccg caacgagcgc aaccctcgtc cactgttgcc    1080
agcaattcgg ttggggactc agtggagacc gccggggtca actcggagga aggtgggat    1140 gacgtcaagt catcatgccc cttatgtcca gggcttcacg catgctacaa tggccggtac    1200
agtgagttgc gacatcgtaa ggtggagcga atctcaaaaa gccggtctca gttcggattg    1260
gggtctgcaa ctcgacctca tgaagtcgga gtcgctagta atcgcagatc agcaacgctg    1320
cggtgaatac gttcccgggg cttgtacaca ccgcccgtca agtcatgaaa gtcggtaaca    1380
```

-continued

```
ctcgaagccg gtggcctaac acttttttgtg ggggagctgt cgaaggtggg actggtgatt    1440
aggactaagt cgtaacaa                                                   1458
```

CUTIBACTERIUM GRANULOSUM STRAIN, AND COMPOSITION COMPRISING SUCH STRAIN OR CULTURE THEREOF FOR PREVENTING OR TREATING ACNE

CROSS-REFERENCE TO RELATED APPLICATIONS

This application is a national phase application of PCT Application No. PCT/KR2019/006241, filed on May 24, 2019, which claims priority to Korean Patent Application No. 10-2018-0098880, filed on Aug. 23, 2018. The entire disclosures of the applications identified in this paragraph are incorporated herein by references.

TECHNICAL FIELD

The present invention relates to a new strain newly isolated, identified and evaluated for its efficacy and its culture. In addition, the present invention relates to a composition comprising such a new strain or its culture. More specifically, the present invention relates to a cosmetic composition having various effects such as skin improvement effect including acne improvement effect and the like, comprising the novel strain or its culture.

BACKGROUND

The inflammatory response in skin begins as an action to defend skin damage when it is caused by physical stimuli or chemicals, bacteria and the like, and a variety of immunocytes and inflammation-inducing cytokines are involved. IL-6 (interleukin-6), IL-8 (interleukin-8), IL-1β (interleukin-β) and the like are representative inflammation-inducing cytokines. IL-1β is a typical cytokine which is produced by an activated mononuclear phagocyte, epithelial cell, or vascular endothelial cell and mediates an inflammatory response, and IL-6 is a cytokine which is released by a T cell and a macrophage and stimulates an immune response and controls an inflammatory response. In addition, the activated macrophage excessively produces nitric oxide (NO) or prostaglandin E2 (PGE2) as well as inflammation-inducing cytokines, thereby further activating the inflammation process. For example, IL-8 expression is induced in various cells such as peripheral blood monocyte, tissue macrophage, NK cell, fibroblast, vascular endothelial cell, and the like, responding to stimulation by inflammatory cytokines.

Inflammatory diseases related to increased (for example, excessive) IL-8 level include inflammatory diseases such as acne, inflammatory keratosis (for example, psoriasis), atopic dermatitis, contact dermatitis, and the like.

Atopic dermatitis (AD) is an inflammatory skin disease accompanying itchiness, and it is chronic and it usually begins in infancy. AD has unceasing itchiness as a major symptom, and has a property of repeating recovery and deterioration without a specific reason. Despite of many recent researches on AD, the cause of AD has not been clearly known until now.

Acne means an inflammatory disease of sebaceous gland of skin. Acne or its acne marks may be caused by bacteria that live in skin, and as same as intestinal bacteria, when the balance is broken, it may cause dermatitis.

*S. aureus* has been known to act on an epidermal cell to destroy a skin barrier function or to act as a superantigen on a T cell to induce an inflammation response.

The research that the colonization and inflammation of the *S. aureus* representatively induces deterioration of atopic dermatitis and eczematous dermatitis and causes asthma and food allergy when progressed as long-term chronic inflammation has been reported. In addition, it has been reported that *S. aureus* was detected in a large amount, in microorganism culturing for patients suffering from skin diseases such as folliculitis, furunculosis, impetigo, paronychia, ecthyma and the like. It has been known that *S. aureus* is clinically related to various inflammatory skin diseases, in addition to atopic diseases (1. Atopic dermatitis and the atopic march. J. Allergy Clin. Immunol. 2003, 2. Antibiotic susceptibility of *Staphylococcus aureus* strains responsible for community-acquired skin infections. Ann Dermatol Venereol. 2008).

On the other hand, lack of filaggrin and modification of filaggrin gene have been well known to be closely related to occurrence and progression of atopic dermatitis.

Filaggrin is a moisturizing component comprised in keratinocytes that make up a skin barrier, and is a protein which plays an important role in formation of stratum corneum together with proteins such as keratin, involucrin, loricrin, and the like. Reduction of the amount of expression of filaggrin causes changes in function and moisturization of the skin barrier and leads to various lesions. In particular, formation of a normal skin barrier plays an important role in defense against external stimuli, and when this function is lost, it plays a key role in progression of atopy. Filaggrin is a target of effective improvement of atopic dermatitis in that the absorption of an antigen through skin is an important factor in the increase of atopic dermatitis.

Furthermore, in a recent research, it has been reported that the abnormality of expression of claudin 1 gene (claudin 1, CDN1) as well as the effect by filaggrin protein of atopic dermatitis patients are closely related to atopic dermatitis.

On the other hand, *Cutibacterium granulosum* has been known as one of skin flora-derived bacteria, and until now, it has been known as a causative bacterium (pathogen) of many infections.

The inventors of the present invention have conducted researches for alleviating acne particularly among various skin diseases, thereby achieving the present invention.

SUMMARY

Technical Problem

Accordingly, in order to solve the above problems, the present invention provides a composition for improving skin conditions using *Cutibacterium granulosum* which has been known only as a pathogen in the past and a novel strain of *Cutibacterium granulosum*.

The present invention provides a use for improvement, treatment or alleviation of acne or inflammatory skin diseases, using *Cutibacterium granulosum* GENSC02 strain or its culture as an active ingredient, or a use for improvement of atopic dermatitis symptoms. The present invention provides a composition for improving, treating or alleviating atopic dermatitis symptoms, acne and inflammatory diseases, comprising *Cutibacterium granulosum* GENSC02 strain or its culture. Specifically, it provides a composition for improving, treating or alleviating inflammatory skin diseases caused by fine dust.

The present invention provides *Cutibacterium granulosum* GENSC02 strain or its culture, and a cosmetic composition comprising thereof, and provides a novel use of *Cutibacterium granulosum* GENSC02 strain or its culture.

The present invention provides a use for inhibition, improvement, treatment or alleviation of inflammatory skin diseases such as atopic dermatitis symptoms, acne or folliculitis, and the like, using *Cutibacterium granulosum* GENSCO2 strain or its culture as an active ingredient. The present invention provides a composition for improvement, treatment or alleviation of acne, folliculitis and inflammatory diseases, comprising *Cutibacterium granulosum* GENSCO2 strain or its culture.

The present invention provides a composition having a skin moisturizing effect through skin barrier enhancement, comprising *Cutibacterium granulosum* GENSCO2 strain or its culture.

Technical Solution

One embodiment of the present invention provides *Cutibacterium granulosum* GENSC02 strain (accession number KCTC 13597BP).

One embodiment of the present invention provides a culture of the *Cutibacterium granulosum* GENSC02 strain (accession number KCTC 13597BP).

Until now, *Cutibacterium granulosum* has been known as a pathogen which causes an infectious disease. However, interestingly, it has been confirmed that the GENSC02 strain or its culture of the present invention not only has no skin toxicity, but also is rather useful for skin condition improvement, thereby completing the present invention.

The strain has an effect of removal or inhibiting formation of biofilm produced by microorganisms, and has an antibacterial activity.

In particular, the strain or culture of the strain has an acne inhibitory activity and may prevent the growth of acne causative bacterium.

According to one embodiment of the present invention, the *Cutibacterium granulosum* GENSC02 strain of the present invention is a microorganism resident in skin, and it has been confirmed that it is a novel strain belonging to *Cutibacterium granulosum* through 16S rDNA sequence analysis and API test. The strain was deposited to Korea Research Institute of Bioscience & Biotechnology Korean Collection for Type Cultures (KCTC) on Jul. 24, 2018 and received Accession number KCTC 13597BP.

According to one embodiment, the *Cutibacterium granulosum* GENSC02 strain or its culture of one embodiment of the present invention may show an antibacterial activity against *Staphylococcus aureus* or *Cutibacterium acnes*.

The colonization and infection of the *S. aureus* and *C. acnes* may cause acne and various skin inflammations. The colonization and infection of the *S. aureus* and *C. acnes* may cause or deteriorate acne, folliculitis or armpit or foot odor, and the like, but the *Cutibacterium granulosum* GENSC02 strain or its culture of the present invention can inhibit the growth of the *S. aureus* and *C. acnes*, and have an antibacterial activity against *S. aureus* and *C. acnes*.

In one embodiment, the *Cutibacterium granulosum* GENSC02 strain or its culture of the present invention can exhibit not only the inhibitory effect of growth of a microorganism, but also the effect of removal or formation-inhibiting of biofilm produced by the microorganism.

In one embodiment, the *Cutibacterium granulosum* GENSC02 strain or its culture may have an activity of inhibiting, improving or treating atopic dermatitis, acne or inflammatory skin diseases. Specifically, a composition for improving, treating or alleviating inflammatory skin diseases by fine dust is to be provided.

In one embodiment, the *Cutibacterium granulosum* GENSC02 strain or its culture has a skin moisturizing activity. In one embodiment, a composition for skin moisturizing comprising the *Cutibacterium granulosum* GENSC02 strain or its culture as an active ingredient may be provided.

In one embodiment, the present invention provides an antibacterial composition comprising the *Cutibacterium granulosum* GENSC02 strain or its culture as an active ingredient.

In one embodiment, the present invention provides a composition for treating, preventing or improving atopic dermatitis, acne or inflammatory skin diseases comprising the *Cutibacterium granulosum* GENSC02 strain or its culture. Specifically, a composition for improving, treating or alleviating inflammatory skin diseases by fine dust is provided.

In one embodiment, the present invention provides a composition for skin moisturizing comprising the *Cutibacterium granulosum* GENSC02 strain or its culture as an active ingredient.

The term "culture" of the present invention means a total medium comprising the strain, strain extract, its metabolite, extra nutriments and the like, obtained by culturing the strain during a certain period in a medium capable of supplying nutriments so that the *Cutibacterium granulosum* GENSC02 strain can grow and survive, but includes a culture solution in which the strain is eliminated after culturing the strain.

The culture solution may mean only the upper layer liquid collected except for the sunken lower layer by leaving it for a certain time, or one in which microbial cells are removed through filtration, or only the upper part of liquid centrifuged to remove the lower part of precipitation. The culture solution may be used as a concentrate by concentration by common methods.

The culture solution or concentrate of the culture solution may be provided as a dried material by drying by common methods.

The "culture" mentioned herein may include a culture solution of a microbial cell, a concentrate of culture solution, a dried material of the culture solution or concentrate, unless otherwise mentioned. The culture may comprise a microbial cell in some cases, and may not comprise it, and the inclusion of a microbial cell is not particularly a problem.

The "microbial cell" means the strain of the present invention itself, and it includes the isolated and selected strain itself or a strain isolated from the culture solution by culturing the strain. The microbial cell may be obtained by collecting the lower sunken part by centrifugation, or may be obtained by leaving it for a certain time and removing the upper liquid, as it is sunken in the lower layer of the culture solution by gravity.

According to one embodiment, the culture of the *Cutibacterium granulosum* GENSC02 strain of the present invention may use a medium easily selected according to a purpose by those skilled in the art among media used for microorganism culturing, and preferably, it may use a medium used for *Cutibacterium* culturing, and more preferably, it may use RCM (Reinforced *Clostridium* Medium) medium, TSB (Tryptic soy broth) or BHI (Brain Heart Infusion) medium, but not limited thereto.

According to one specific embodiment of the present invention, the culture of the *Cutibacterium granulosum* GENSC02 strain of the present invention may be prepared by inoculating the strain of the present invention in the microorganism culturing medium by microorganism culturing methods known in the art (for example, standing culturing, etc.).

The culture of the *Cutibacterium granulosum* GENSC02 strain may include a culture solution or a concentrate of the culture solution, and a dried material thereof, and the concentrate or dried material may be easily prepared by concentration or drying methods of a microorganism or culture solution known in the art.

According to one embodiment of the present invention, a composition comprising *Cutibacterium granulosum* GENSC02 strain or its culture, and preferably, a cosmetic composition, a food composition or a pharmaceutical composition is provided.

The cosmetic composition or pharmaceutical composition may be used as a skin external preparation, and it may be directly applied to an affected area. For example, it may be prepared in various forms such as ointment, cream, emulsion and the like.

In other embodiment, the pharmaceutical composition may be absorbed in the body by oral or parenteral administration, and for example, it may be administered in a non-limiting form such as powders, granules, capsules, injections and the like. The form of the cosmetic composition or pharmaceutical composition is not particularly limited.

The cosmetic composition may inhibit or improve atopic dermatitis or inflammatory skin diseases, and may be effective in removal or reduction of body odor (for example, foot odor, armpit odor).

The examples of the inflammatory skin diseases include inflammatory keratosis (for example, psoriasis), folliculitis, bacterial dermatitis, impetigo, folliculitis alopecia and the like.

The cosmetic composition according to one embodiment of the present invention may intensify skin barriers and enhance skin moisturizing. In other words, one embodiment of the present invention provides a composition for skin moisturizing comprising the *Cutibacterium granulosum* GENSC02 strain (KCTC 13597BP) or culture of the strain.

The cosmetic composition may have an antibacterial activity against *Staphylococcus aureus* or *Cutibacterium acnes*. Thus, one embodiment of the present invention provides an antibacterial composition comprising the *Cutibacterium granulosum* GENSC02 strain (KCTC 13597BP) or culture of the strain.

Advantageous Effects

The present invention provides a novel strain of *Cutibacterium granulosum* which is excellent for acne improvement. In addition, it has an excellent effect of improvement of atopic symptoms.

The present invention has confirmed a novel strain of *Cutibacterium granulosum*, and has discovered the effect of improvement of skin symptoms using the strain or its culture. Accordingly, the present invention can provide a new strain of *Cutibacterium granulosum*, having a skin improvement function. In addition, the present invention provides a composition for improving atopic dermatitis and acne, improving inflammatory skin diseases such as inflammatory keratosis, folliculitis, bacterial dermatitis, impetigo, folliculitis alopecia, and the like, and inhibitory treating or alleviating foot odor or armpit odor, comprising a novel strain of *Cutibacterium granulosum* or its culture. Furthermore, the present invention provides a cosmetic composition for skin moisturizing comprising a novel strain of *Cutibacterium granulosum* or its culture. The present invention provides a cosmetic composition for alleviating skin inflammation by fine dust comprising a novel strain of *Cutibacterium granulosum* or its culture.

BRIEF DESCRIPTION OF DRAWINGS

FIG. 1 shows the 16s rRNA sequence of *Cutibacterium granulosum* GENSCO2 strain (Accession number: KCTC 13597BP) of the present invention.

DETAILED DESCRIPTION

Figure 2:
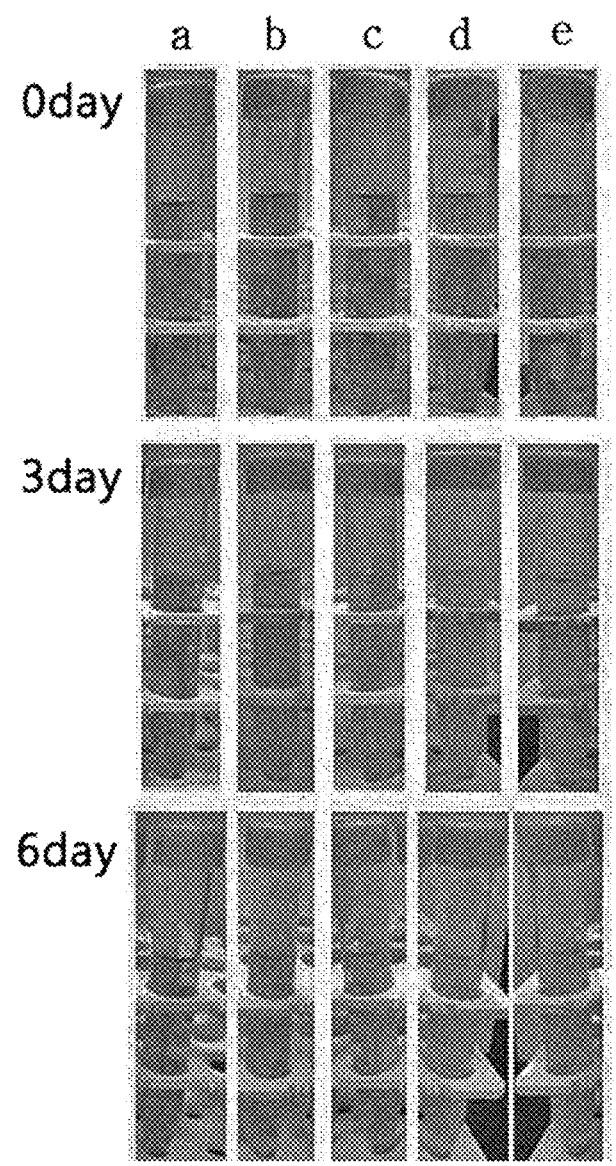
FIG. 2 shows the color change according to the use of glycerol by each *C. granulosum* strain (color change at days 0, 3 and 6).

Hereinafter, the present invention will be described by the following examples and the like in order to described it more specifically. However, the examples according to the present invention may be modified to various other forms, and the scope of the present invention should not be construed as being limited to the examples described below. The examples of the present invention are illustratively provided in order to facilitate a specific understanding of the present invention.

[Example 1] Isolation and Identification of *Cutibacteria granulosum* GENSC02

1-1. Isolation of Strain

Skin-derived bacteria isolation was carried out from adults who have never had skin diseases such as atopy, psoriasis or acne and the like, or who have not had a history of treatment related to it in the past 6 months. To collect skin samples, unwashed both cheeks and ala nasi were rubbed with a sterile swab dampened with sterilized water by applying a force. The swab was immediately sealed in a test tube containing Reinforced Clostridial Medium (RCM), and the test tube was filled with nitrogen and incubated at 37° C. for 48 to 72 hours. The medium of the test tube containing the cultured swab was steaked on an RCM agar plate by picking it with a platinum loop, and this procedure was repeated 3-4 times to separate pure colonies.

1-2. Identification of Strain

1) Biological Identification Using API Kit

As a method for biochemically identifying an isolated strain, an anaerobic bacterium API 20A kit (biomerieux Co., France) was used. After culturing at 37° C. for 24 hours in a RCM liquid medium of 10 ml and then centrifuging, the medium was removed. After washing with PBS 2-3 times and then $OD_{600}$=3 resuspending with a medium comprised in a kit according to the protocol provided by the manufacturer, it was aliquoted in an appropriate amount to each well of API 20A kit and was anaerobically cultured at 37° C. for 24 hours and then was read.

The final result was identified in a program for identification, API web, and the result was shown in the following Table 1. As the result of identification of API 20A, it showed the same biochemical properties as *Propionibacterium* (=*Cutibacterium*) *granulosum*.

The API 20A reading result was shown in the following Table 1.

TABLE 1

| No | Carbohydrates | Utilized |
| --- | --- | --- |
| 0 | L-tryptophane | − |
| 1 | urea | − |
| 2 | D-glucose | + |
| 3 | D-mannitol | − |
| 4 | D-lactose (bovine origin) | − |
| 5 | D-saccharose (sucrose) | + |
| 6 | D-maltose | + |
| 7 | salicin | − |
| 8 | D-xylose | − |
| 9 | L-arabinose | − |
| 10 | gelatin (bovine origin) | − |
| 11 | esculin ferric citrate | − |

TABLE 1-continued

| No | Carbohydrates | Utilized |
| --- | --- | --- |
| 12 | glycerol | + |
| 13 | D-cellobiose | − |
| 14 | D-mannose | + |
| 15 | D-melezitose | − |
| 16 | D-raffinose | − |
| 17 | D-sorbitol | − |
| 18 | L-rhamnose | − |
| 19 | D-trehalose | + |

2) A 16s RNA gene sequence was determined by collecting 1 ml of pure culture solution of the identified and isolated strain through a 16s rRNA gene sequence and requesting to Macrogen. Primers for PCR were universal primers of 16s rRNA gene, 27F (5'-AGAGTTT-GATCMTGGCTCAG-3') and 1492R (5'-TACGGYTA-CCTTGTTACGACTT-3'), and 785F (5'-GGATTAGA-TACCCTGGTA-3') and 907R (5'-CCGTCAATTCMTT-TRAGTTT-3') were used for sequencing. The 16s rRNA sequence of the isolated strain was shown in FIG. 1. Based on the above result, the strain was named "*Cutibacterium granulosum* GENSC02" strain, and it was deposited to Korea Research Institute of Bioscience & Biotechnology Korean Collection for Type Cultures (KCTC) on Jul. 24, 2018 and received Accession number KCTC13597BP.

1-3. Classification of Strains by Glycerol Use

In order to confirm differences from other strains of the same kind with the deposited strain, the glycerol use was confirmed.

To confirm the glycerol use, a medium was prepared by adding 2% glycerol to rich media (10 g/L yeast extract, 5 g/L TSB media, 2.5 g/L $K_2HPO_4$ and 1.5 g/l $KH_2PO_4$). In addition, when the inoculated medium used glycerol, the color of the medium changed from red to yellow, and therefore, 0.001% (w/v) of phenol red was added to visibly determine the use. Each of bacteria was inoculated in an RCM medium at $10^5$ CFU/ml through the active state and was anaerobically cultured at 37° C., and the medium inoculated with none was stored under the same conditions to clearly check the color change. The aspect of the change was observed at the same time for 6 days.

As a result, from the 3rd day of culture, the color began to change in NSM13-4, CSM1-3 and CSM5-1, and the red color disappeared as time progressed, indicating perfect yellow color after 4-5 days. On the other hand, GENSC02 was slightly reddish compared to that before incubation, but the color difference was low compared to the control. Thus, it was confirmed that GENSC02 had a characteristic of little or no use of glycerol under rich media, and this means that the ability of using glycerol differs depending on the culture media such as rich media, API 20A media and the like.

Table 2 shows the glycerol use result by each strain. As it turns yellow, it was marked as −/+/++/+++. In addition, the color change depending on glycerol use by each *C. granulosum* strain was shown in FIG. 2. (color change at day 1. 3 and 6). Thus, it was confirmed that GENSC02 has a difference from other stains in the ability of using glycerol.

TABLE 2

| | Strain | Species | 0 day | 1 day | 2 days | 3 days | 4 days | 5 days | 6 days |
| --- | --- | --- | --- | --- | --- | --- | --- | --- | --- |
| a | control | | − | − | − | − | − | − | − |
| b | GENSC02 | *C. granulosum* | − | − | − | − | − | − | − |
| c | NSM13-4 | *C. granulosum* | − | − | − | + | ++ | ++ | ++ |
| d | CSM1-3 | *C. granulosum* | − | − | − | ++ | ++ | +++ | +++ |
| e | CSM5-1 | *C. granulosum* | − | − | − | + | ++ | ++ | ++ |

[Example 2] Hemolysis Test of *Cutibacteria granulosum* GENSC02

Figure 3:
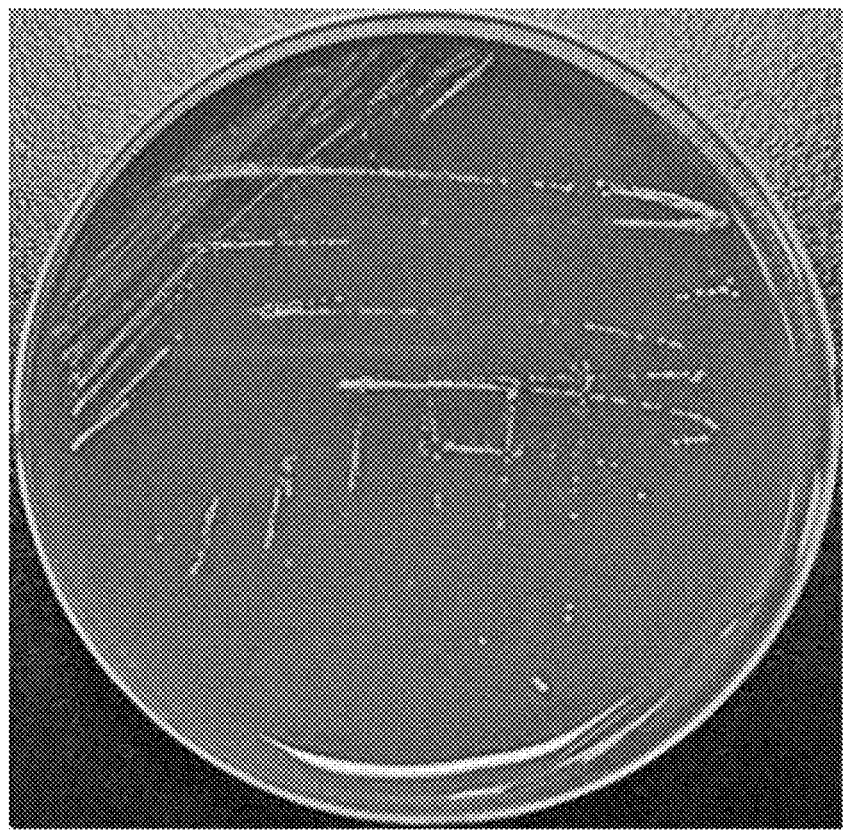
FIG. 3 shows the result of smearing the *Cutibacterium granulosum* GENSCO2 strain of the present invention on sheep blood agar and culturing it. No transparent ring was found around the microbial cell, and thereby it can be seen that it is not harmful to the human body because there is no hemolysis.

A considerable number of *Cutibacterium granulosum* strains have hemolytic toxicity and are harmful to the human body depending on strains. To confirm the safety of *Cutibacterium granulosum* GENSC02, the presence or absence of hemolytic toxicity was confirmed. The *Cutibacterium granulosum* GENSC02 purely cultured in a liquid medium was collected by a platinum loop and it was streaked on a sheep blood agar and it was anaerobically cultured at 37° C. for 48 hours. The hemolysis was determined by the presence of transparent rings around microbial cells, and it was determined that *Cutibacterium granulosum* GENSC02 had no hemolysis for sheep blood and therefore it was not harmful to the human body, as could be seen in FIG. 3.

[Example 3] Growth Inhibition on *Staphylococcus aureus* KCTC 1621 and *Cutibacterium acnes* ATCC 6919 (Overlay Clear Zone Test)

Figure 4:
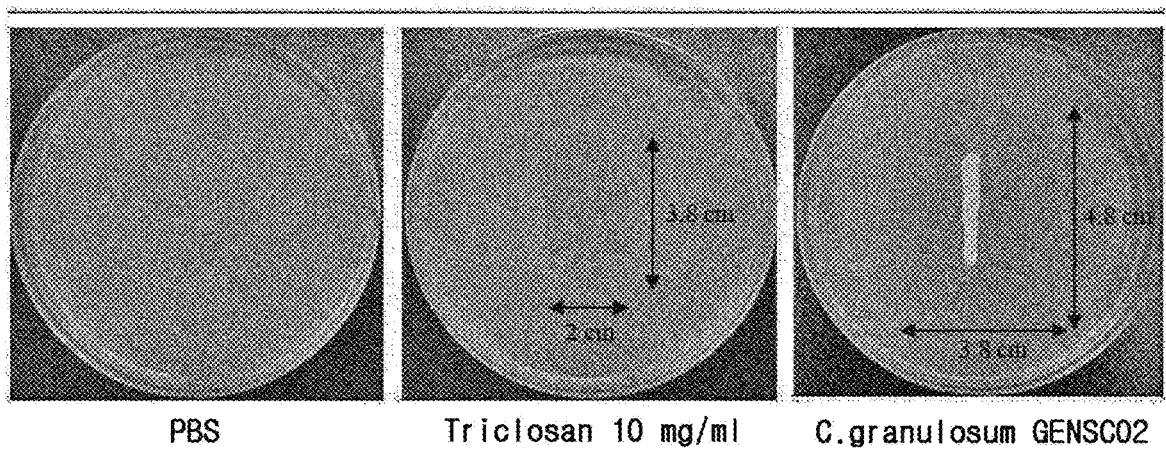
FIG. 4 shows the result of inhibiting the growth for *Staphylococcus aureus* KCTC 1621 by *Cutibacterium granulosum* GENSCO2 strain.

The effect of growth inhibition of *S. aureus* and *C. acnes* was confirmed by observing formation of a clear zone. When these bacteria are inoculated on an agar medium, bacteria grow in a light color, and therefore the color of the medium becomes cloudy, and it looks transparent if it does not grow. The experiment was progressed, expecting that *S. aureus* and *C. acnes* around *Cutibacterium granulosum* GENSC02 could not grow and they became transparent, if *Cutibacterium granulosum* GENSC02 had the effect of inhibiting the growth of bacteria. The *Cutibacterium granulosum* GENSC02 culture broth was collected with a platinum loop and was anaerobically cultured in a thin RCM agar plate at 37° C. for 72 hours by drawing a line about 2.5 cm. After confirming that *Cutibacterium granulosum* GENSC02 sufficiently grew, *S. aureus* and *C. acnes* strains adjusted to $10^4$ cfu/ml were inoculated in 10 ml RCM agar at about 45° C. which was not yet solidified, and they were well suspended before the medium was hardened, and they were evenly solidified by pouring them on the agar plate in which *Cutibacterium granulosum* GENSC02 grew. In the solidified agar plate, *S. aureus* and *C. acnes* were further cultured anaerobically at 37° C. for about 40 hours and about 72 hours, respectively, to observe the size of the clear zone appearing around *Cutibacterium granulosum* GENSC02. As the negative control group, phosphate-buffered saline (PBS) was used, and as the positive control group, triclosan was used, and *S. aureus* and *C. acnes* were treated at an amount of 10 mg/ml and 200 mg/ml, respectively. As a result, as FIG. 4, the transparent area around the *Cutibacterium granulosum* GENSC02 was observed, and the transparency was reduced with distance from *Cutibacterium granulosum* GENSC02, thereby confirming that the *Cutibacterium granulosum* GENSC02 had an ability of inhibiting growth of *S. aureus*. It could be seen that when treating the negative control group, PBS, the clear zone was not observed, and when treating a bactericide, triclosan as the positive control group, the clear zone was observed, but it had much smaller area than GENSC02 treatment. The result was shown in FIG. 4.

Figure 5:
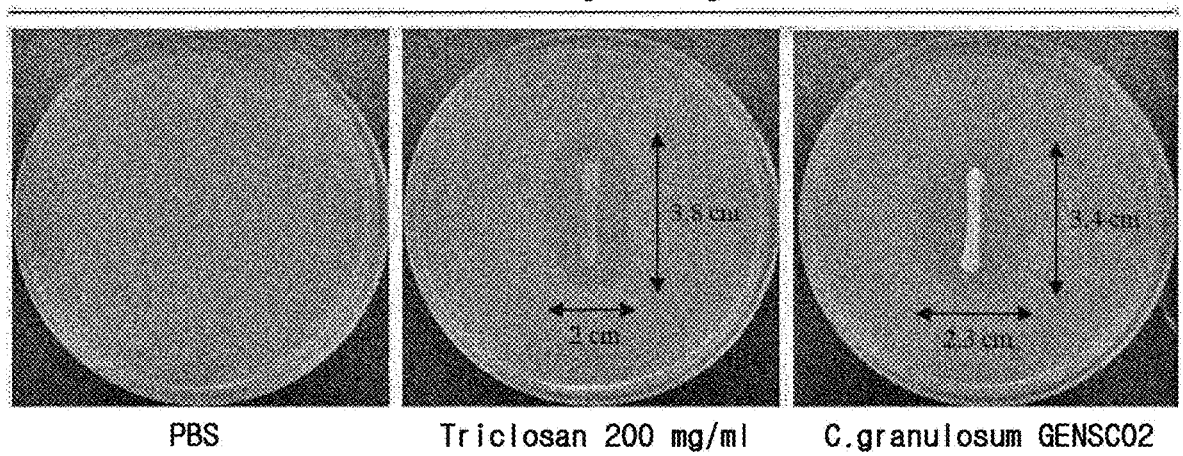
FIG. 5 shows the result of inhibiting the growth for *Cutibacterium acnes* ATCC 6919 by *Cutibacterium granulosum* GENSCO2 strain.

In addition, as could be seen in FIG. 5, in the result of inoculating *C. acnes*, the transparent area around the *Cutibacterium granulosum* GENSC02 was observed, and the transparency was reduced with distance from *Cutibacterium granulosum* GENSC02, thereby confirming that the *Cutibacterium granulosum* GENSC02 had an ability of inhibiting growth of *C. acnes*. Also, it could be seen that when treating the negative control group, PBS, the clear zone was not observed, and when treating a bactericide, triclosan as the positive control group, the clear zone was observed, but it had much smaller area than GENSC02 treatment.

Through these results, it was confirmed that the *Cutibacterium granulosum* GENSC02 of the present invention could provide an effect of improving, preventing or treating acne by inhibiting an acne-causing bacterium, *C. acnes*.

[Example 4] Preparation of Fermented Filtrates of the Strain of the Present Invention

*Cutibacterium granulosum* GENSC02 strain was anaerobically cultured on a RCM agar plate at 37° C. for 72 hours. Single colony shown in a solid medium was subcultured in an RCM liquid medium of 10 ml and was cultured under the same condition. 72 hours later, 0.1% was inoculated to the same liquid medium, and it was cultured for 72 hours under the same condition, and the supernatant was centrifuged and filtrated with a 0.22 um pore size filter.

[Example 5] Anti-Inflammatory Efficacy Evaluation (Selection of Beneficial Bacteria)

At first, fermented filtrates of *C. granulosum* strain were pre-treated for 1 hour to cells in which $2 \times 10^5$ of HaCaT human keratinocyte lines were attached in a 6-well plate, respectively, by culturing them in a 37° C. and 5% $CO_2$ incubator for 24 hours. Then, the heat-treated *C. acnes* (100MOI) was treated and was reacted for 4 hours. Then, after extracting RNA for each sample, the RNA expression for one of inflammation response cytokine factors, IL-6 was confirmed by real-time PCR.

Figure 6:
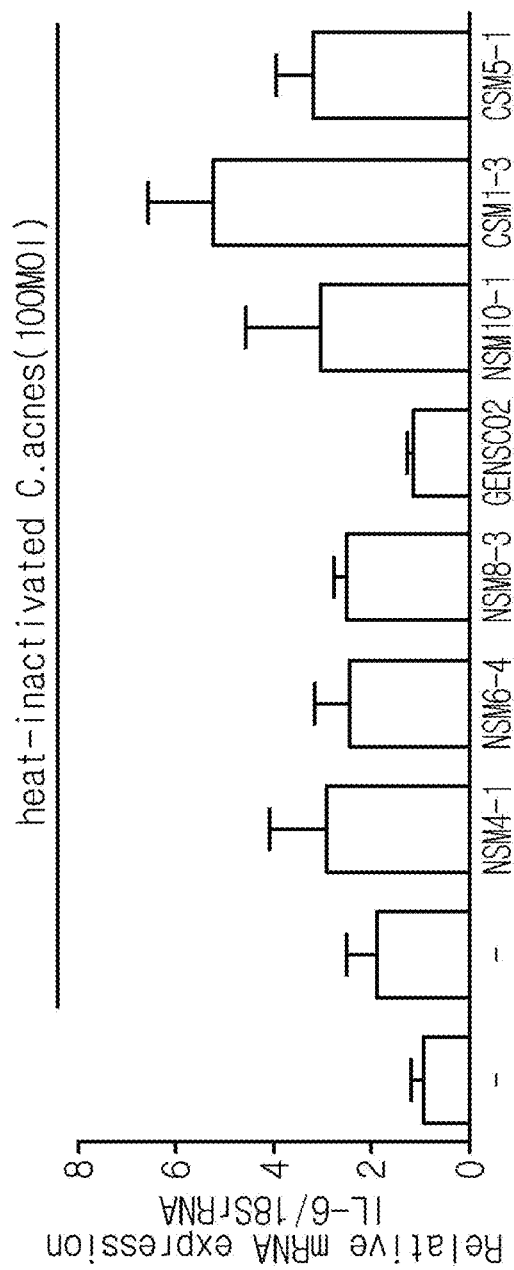
FIG. 6 shows the result of confirming the expression of IL-6 by strain, and IL-6 expression of GENSCO2 was observed as the lowest.

In the result of FIG. 6, it could be seen that inflammation was caused by increases of expression of IL-6 by *C. acnes*. In the comparative experiment with various strains, it was shown that the expression of IL-6 by GENSCO2 fermented filtrates was reduced, and it was confirmed that GENSCO2 had a more excellent anti-inflammatory efficacy than other strains. FIG. 6 shows the result of confirming the expression of IL-6 by strain, and the IL-6 expression of GENSCO2 was observed as the lowest.

Through the result of FIG. 6, in order to investigate the anti-inflammatory efficacy depending on the content of fermented filtrates of GENSCO2, the same experimental procedure as the above experiment was progressed, and the anti-inflammatory efficacy was reproduced again by treating the GENSCO2 fermented filtrates to be pre-treated at a concentration of 0.01, 0.1, and 1%, respectively.

Figure 7:
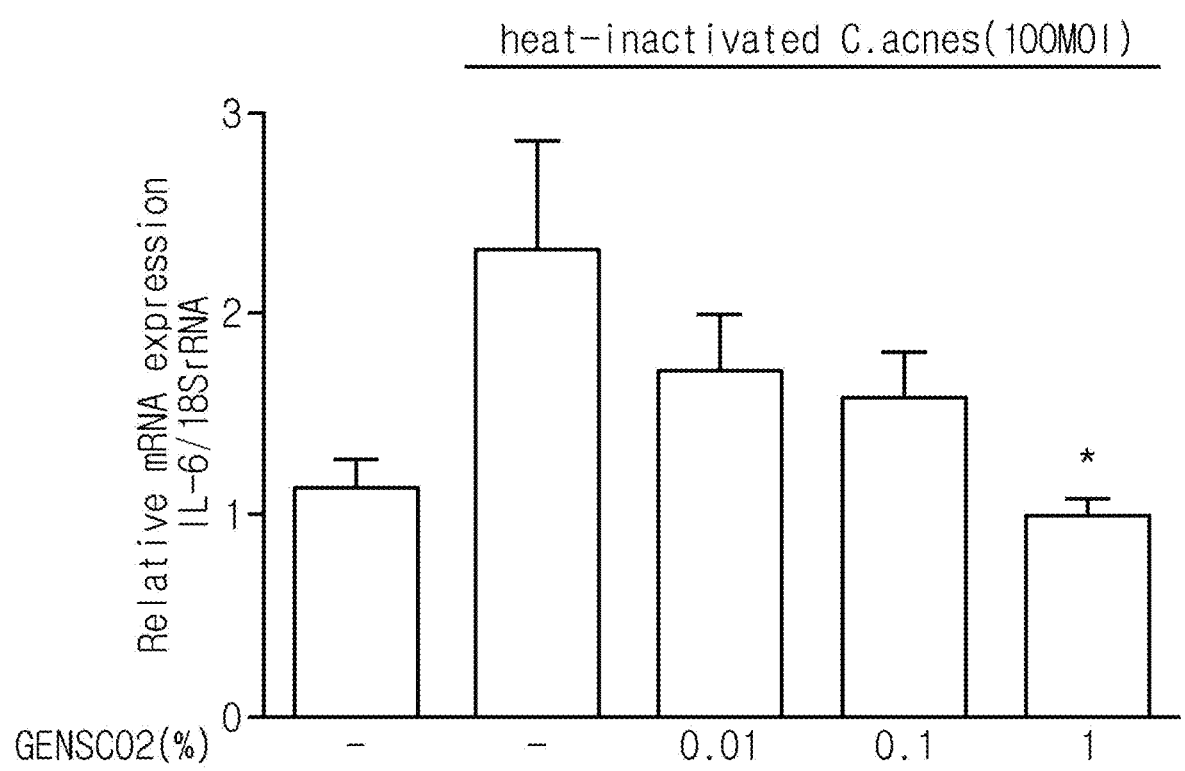
FIG. 7 is the result showing the inhibitory activity of IL-6 expression of the fermented filtrates of GENSCO2 strain by concentration.
Figure 8:
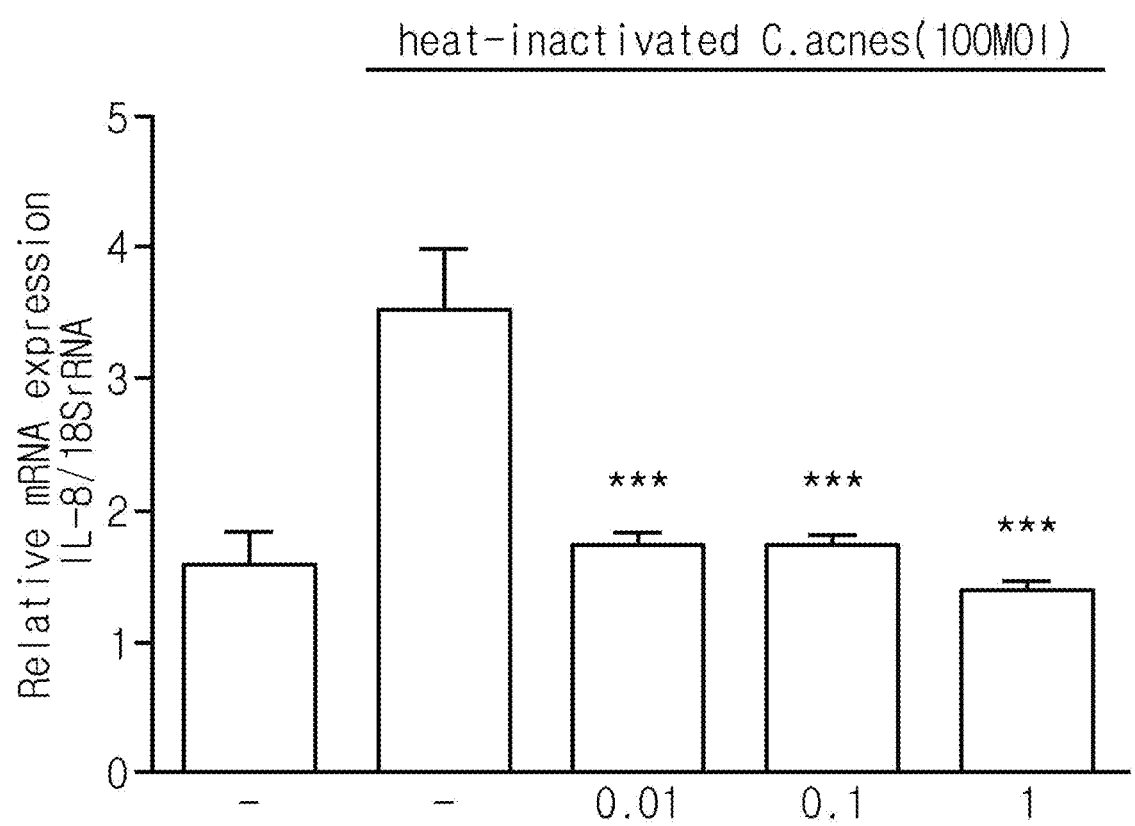
FIG. 8 is the result showing the inhibitory activity of IL-8 expression of the fermented filtrates of GENSCO2 strain by concentration.
Figure 9:
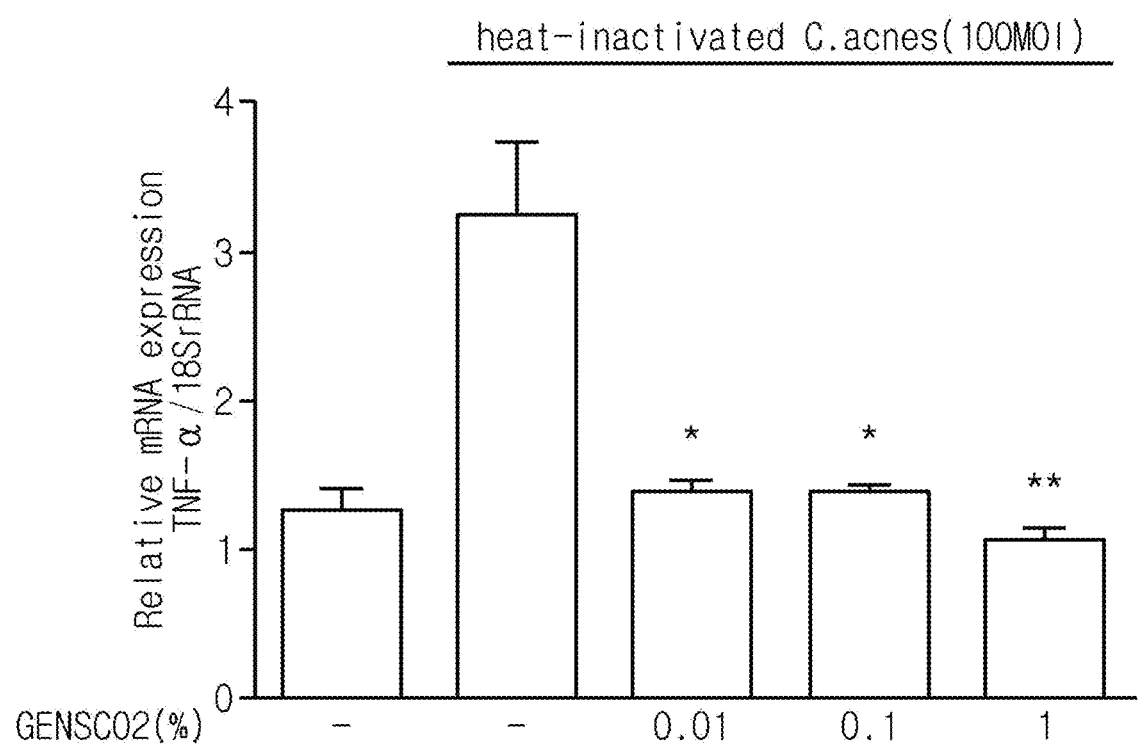
FIG. 9 is the result showing the inhibitory activity of TNF-alpha expression of the fermented filtrates of GENSCO2 by concentration.

In the result of FIG. 7 to FIG. 9, it could be seen that the inflammation by *C. acnes* was caused by increases of expression of IL-6, IL-8, and TNF-α. It was confirmed that the expression of IL-6 was gradually reduced depending on the GENSCO2 fermented filtrates and the expression of IL-8 and TNF-alpha had an excellent anti-inflammatory efficacy in the low content of GENSCO2 fermented filtrates.

[Example 6] Cytotoxicity Confirmation

To evaluate the cytotoxicity of fermented filtrates prepared in the Example 4, the following experiment was progressed. HaCaT cells were attached on a 96-well cell culture plate for 24 hours at $5 \times 10^3$ cells/well each and then the test group samples were added by concentration to culture it under the condition of 5% $CO_2$ and 37° C. for 48 hours. 48 hours later, the cultured cell medium was removed, and 0.5 mg/ml dimethylthiazol-2-yl)-2-5-diphenyltetrazolium bromide (MTT) formazan solution was treated to cells, and they were reacted for 4 hours, and after the time passage, all the cell medium was removed and the formazan solution was dissolved by DMSO and then the absorbance was measured at 570 nm with SpectraMax M2. Then, the survival rate of the HaCaT cell line was calculated by converting with the equation of $O.D_{sample}/O.D_{control} \times 100$.

Figure 10:
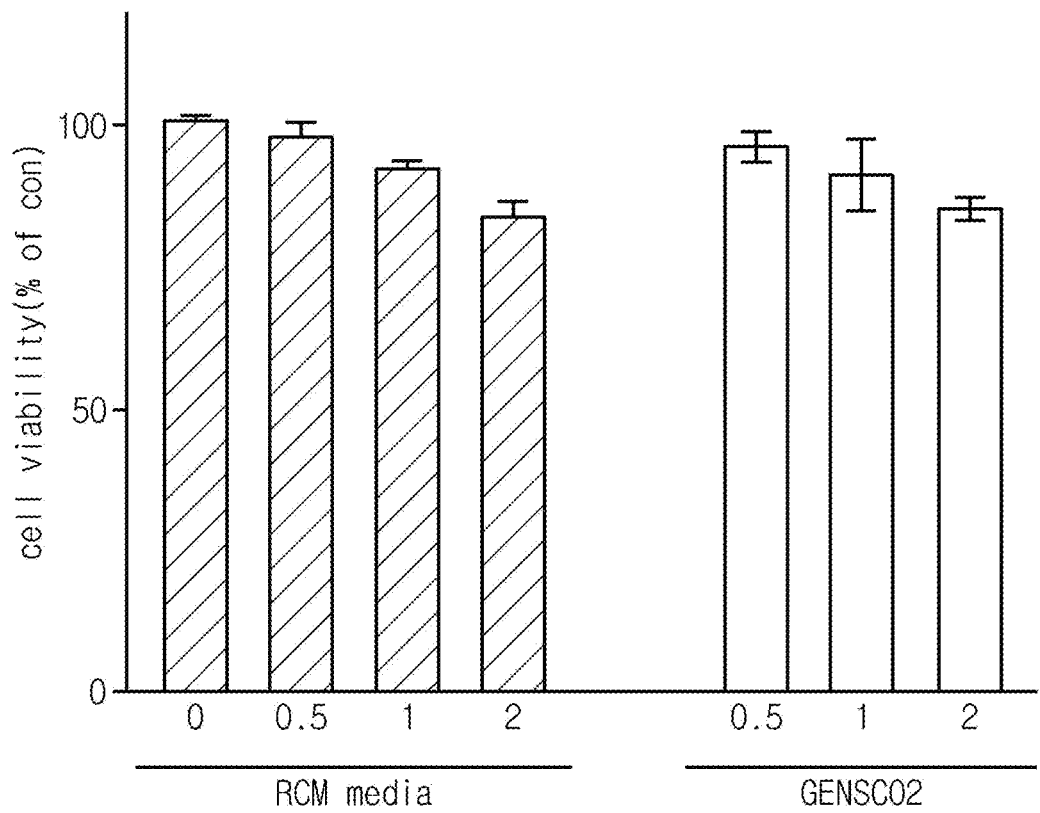
FIG. 10 shows the result of cytotoxicity test of the fermented filtrates of GENSCO2 strain of the present invention.

The cytotoxicity test result of the fermented filtrates was shown in FIG. 10. As could be seen in FIG. 10, the treatment of GENSCO2 did not significantly affect the survival rate of HaCaT cell lines. Thus, it can be seen that GENSCO2 has no cytotoxicity.

[Example 7] Confirmation of Skin Barrier Function Enhancement Efficacy

In order to investigate the GENSCO2 fermented filtrates had a function of skin barrier enhancement for the HaCaT cell line, in addition to the inflammation response, the fermented filtrates of GENSCO2 were treated to the HaCaT cell line by % to the cell culture solution, and then were reacted for 24 hours to confirm the expression of filaggrin and claudin-1 which were markers of the skin barrier function on RNA.

Figure 11:
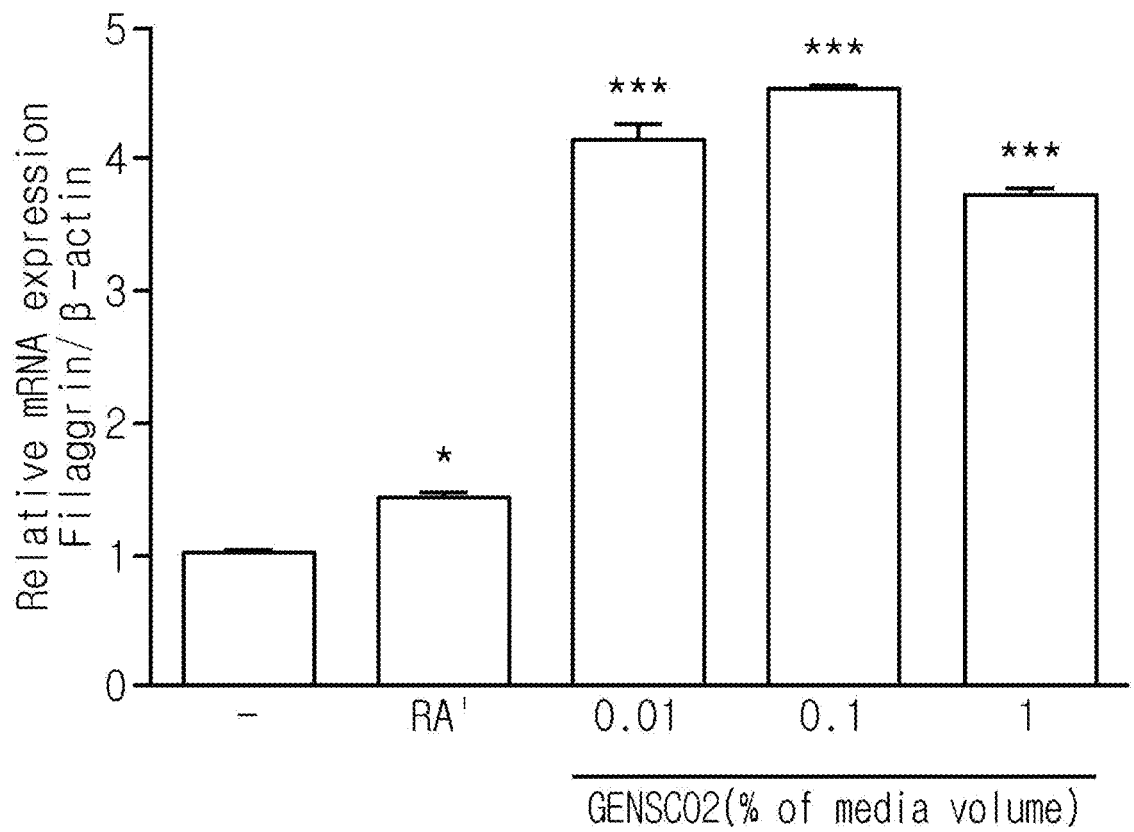
FIG. 11 shows the result of enhanced filaggrin expression by treatment of the fermented filtrates of GENSCO2 strain.
Figure 12:
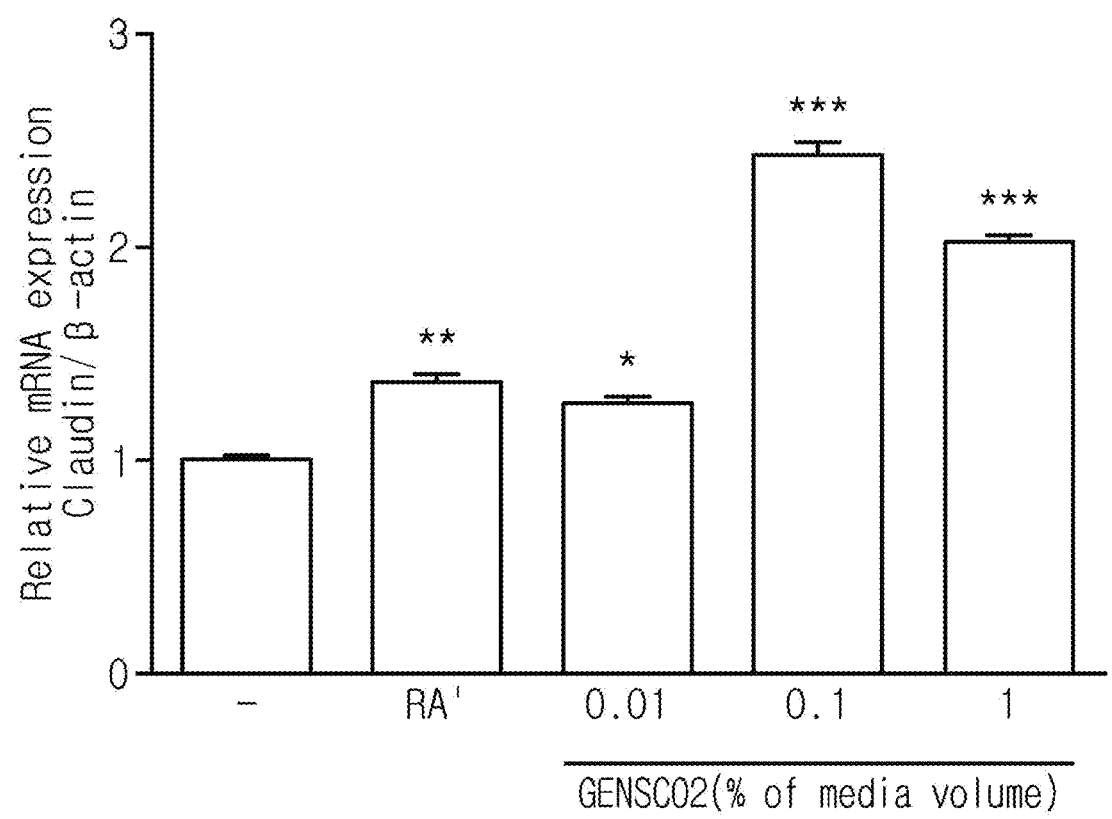
FIG. 12 shows the result of enhanced claudin 1 expression by treatment of the fermented filtrates of GENSCO2 strain.

In the results of FIG. 11 and FIG. 12, it was confirmed that the expression of filaggrin and claudin-1 was increased to 1.5 times by the positive control group, retinoic acid (RA', 1 μM), but on the other hand, the expression of claudin was increased 2 times or more from 0.1% of the GENSCO2 fermented filtrates, and the expression of filaggrin was increased from 0.01% of the GENSCO2 fermented filtrates.

Specifically, as can be seen in FIG. 11, it can be seen that GENSCO2 has an excellent filaggrin expression effect compared than retinoic acid (positive control group) known to have an excellent filaggrin expression effect. Through this, GENSCO2 can provide an atopic dermatitis improvement effect, an acne improvement effect, a skin barrier enhancement effect, and a skin moisture content maintenance or increase effect by increasing filaggrin expression.

As can be seen in FIG. 12, it can be seen that GENSCO2 has an excellent claudin expression effect compared than retinoic acid (positive control group) known to have an excellent filaggrin expression effect. Through this, GENSCO2 can provide an atopic dermatitis improvement effect, an acne improvement effect, a skin barrier enhancement effect, and a skin moisture content maintenance or increase effect by increasing filaggrin expression.

[Example 8] Skin Moisturizing Function Enhancement Efficacy Confirmation

To investigate a function for a skin moisturizing effect by GENSCO2 fermented filtrates, it was confirmed that the fermented filtrates of GENSCO2 were treated to the HaCaT cell line by % to the cell culture solution, and then were reacted for 24 hours to confirm the expression of HAS3 (hyaluronic acid synthase) and aquaporin which were markers of the skin moisturizing function on RNA.

Figure 13:
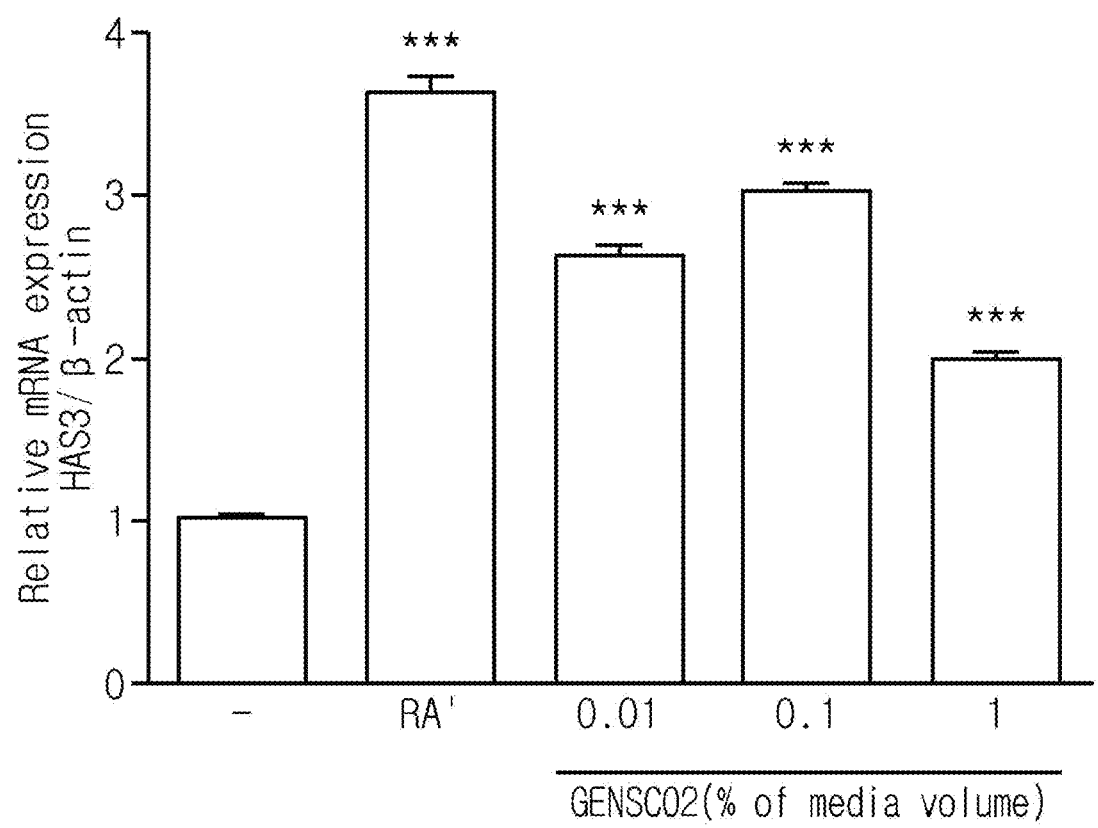
FIG. 13 shows the result of enhanced HAS3 (Hyaluronic acid Synthase) expression by treatment of the fermented filtrates of GENSCO2 strain.
Figure 14:
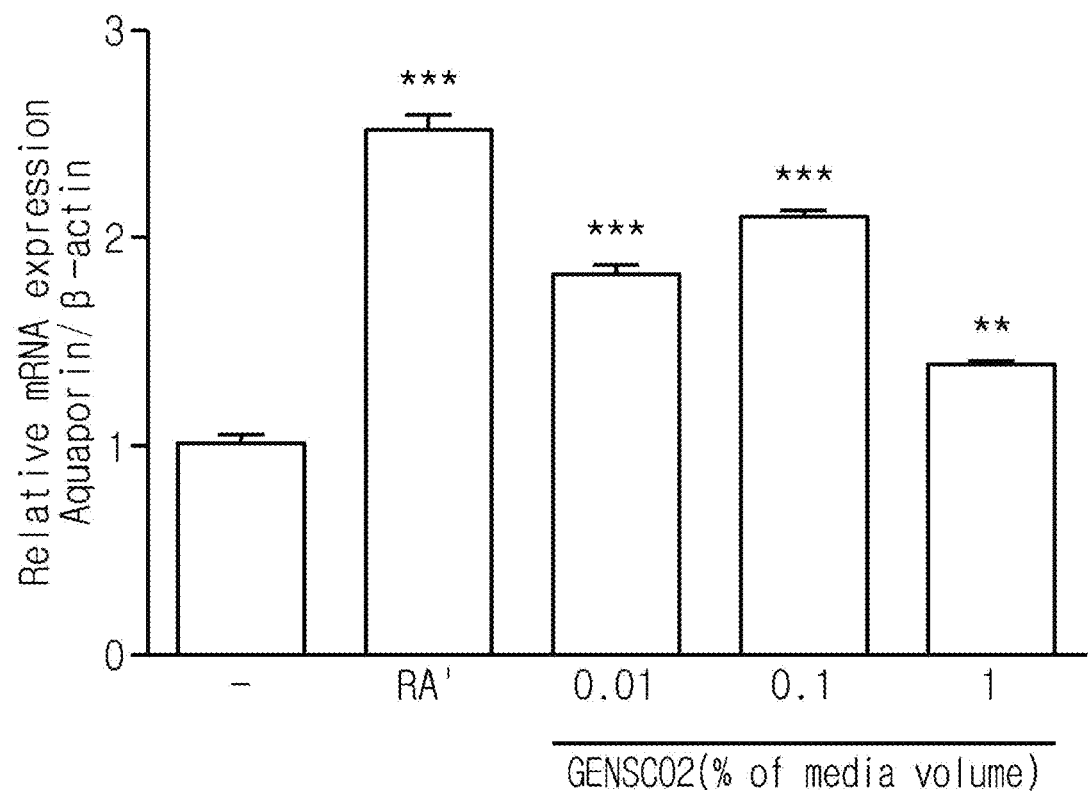
FIG. 14 shows the result of enhanced aquaporin expression by treatment of the fermented filtrates of GENSCO2 strain.

In the results of FIG. 13 and FIG. 14, it was confirmed that the expression of HAS3 (hyaluronic acid synthase) and aquaporin was increased to 2~4 times by the positive control group, retinoic acid (RA', 1 μM), and the expression of HAS3 (hyaluronic acid synthase) and aquaporin was increased to 2 times or more compared to the negative control group (− group) by the fermented filtrates. Based on the results of FIG. 13 and FIG. 14, it was confirmed that GENSCO2 enhanced the function of skin moisturizing.

[Example 9] Measurement of Inhibitory Effect of Formation of Biofilm

A *Staphylococcus aureus* strain (*Staphylococcus aureus* KCTC 1621) was liquid cultured in a titration medium (TSB+0.2% glucose) for 16 to 24 hours. After adding TSB with 0.2% glucose on a 6-well plate (polystyrene), a test group was added to each well in an approximately 5~10% volume. Then, the cultured bacterial solution was inoculated to each well so that the final strain concentration was to be $2 \times 10^6$ CFU/well. Then, it was under static culturing in a 37° C. incubator for 24 hours. After culturing, the culture solution was eliminated and each well was washed twice using sterile PBS of 1~2 ml. After washing, PBS of 2 ml was added and the biofilm was scraped out with a scraper and was suspended, and then the absorbance was measured at 600 nm. The absorbance measurement was conducted using BioPhotometer D30. Untreated wells were used as the negative control group and wells inoculated with baicalein (25 μm/ml) were used as the positive control group to calculate biofilm formation inhibitory ability.

Figure 15:
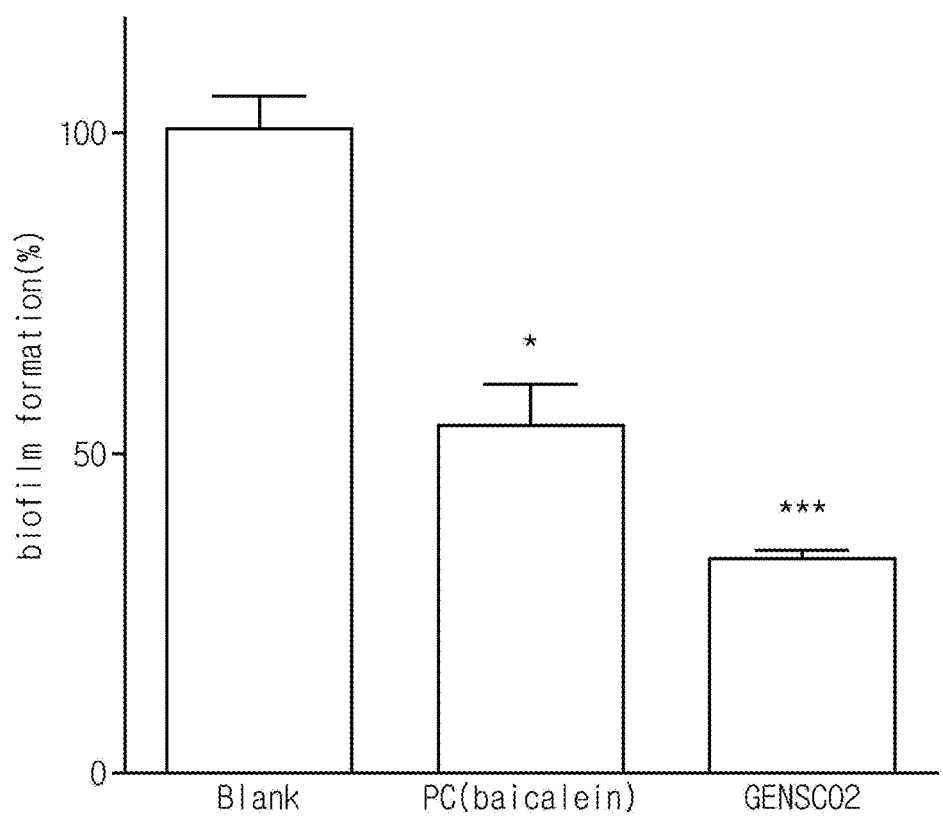
FIG. 15 is the result showing that the biofilm formation-inhibiting effect was excellent by treatment of the fermented filtrates of GENSCO2 strain.

As FIG. 15, it can be seen that GENSCO2 strain has a better biofilm formation inhibitory ability than the positive control group.

[Example 10] Confirmation of Itchiness Alleviation Efficacy

Figure 16:
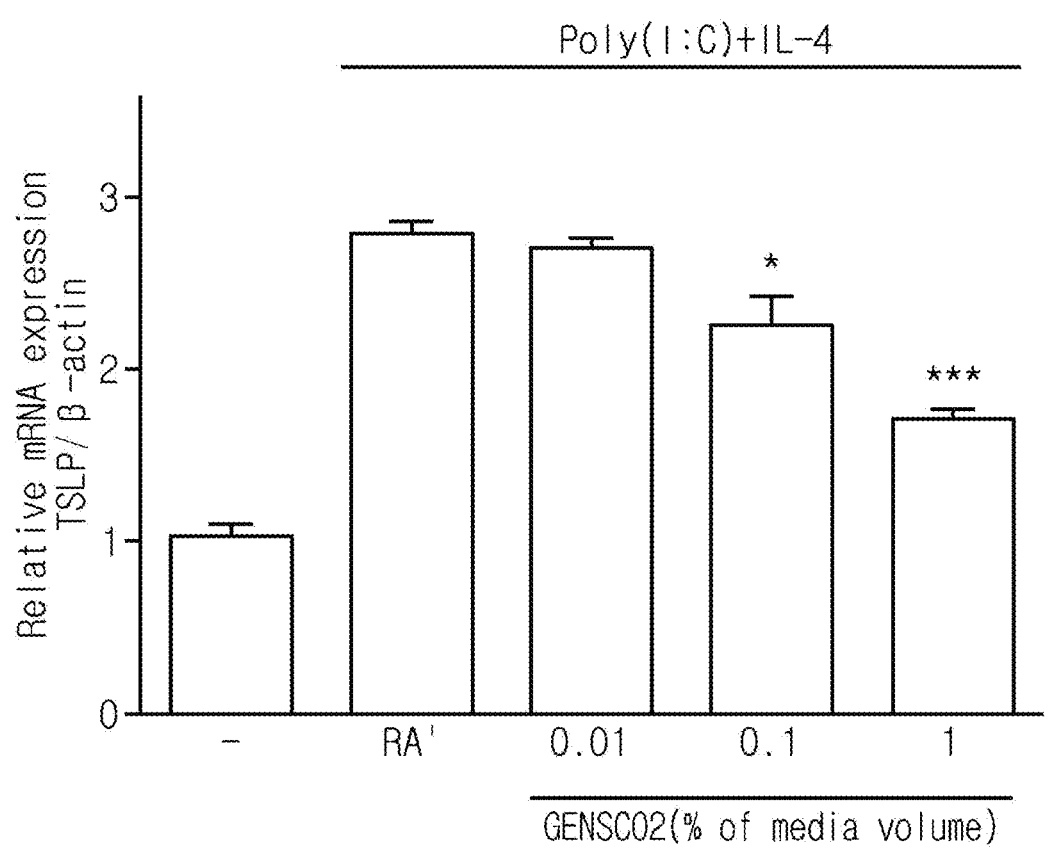
FIG. 16 is the result showing the reduction of TSLP expression by the fermented filtrates of *Cutibacterium granulosum* GENSCO2 strain.

The expression of TSLP, the cytokine acting as one of causes of atopic dermatitis was confirmed on RNA, by treating fermented filtrates of GENSCO2 to the HaCaT cell line by % and then reacting for 4 hours. As shown in FIG. 16, it was confirmed that the TSLP expression degree of fermented filtrates was reduced. Thus, it was confirmed that the GENSCO2 culture of the present invention inhibited the TSLP expression and solved skin itchiness, thereby having an effect in improvement of atopic dermatitis.

[Example 11] *Cutibacterium acnes* ATCC 6919 Lipase Inhibitory Activity (4-Methyl Umbelliferyl Oleate (MUO) Assay)

The lipase inhibitory activity was evaluated using 4-methylumbelliferyl oleate as a substrate. In other words, the positive control group, ketoconazole (2.5 μg/ml), the negative group, and the fermented filtrates were treated to *C. acnes* in RCM broth ($OD_{600}=1$) as 1:1, respectively, and they were anaerobically cultured at 37° C. The 100 ul of supernatant obtained by centrifuging them and 100 ul of 4-MU oleate (0.2 mg/ml in DMSO) were mixed in black 96-well microtiter plates, and they were reacted at 37° C. for 24 hours. The 4-methylumbelliferone released by lipase was measured with a fluorometric microplate reader.

Figure 17:
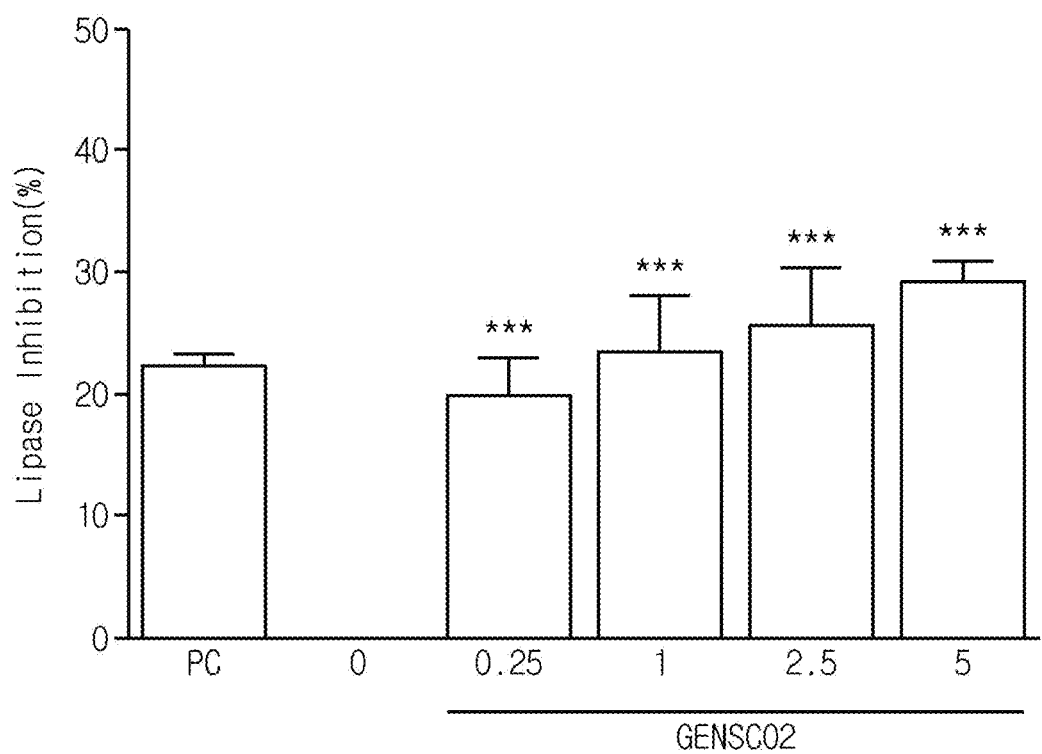
FIG. 17 shows the inhibitory activity of *Cutibacterium acnes* ATCC 6919 lipase by the fermented filtrates of *Cutibacterium granulosum* GENSCO2 strain.

In the result of FIG. 17, it was confirmed that the similar effect to the positive control group was obtained when treating 1% of fermented filtrates, and the *Cutibacterium acnes* ATCC 6919 lipase inhibitory activity was shown in a concentration dependent manner.

[Example 12] Evaluation of Anti-Inflammatory Efficacy Against Fine Dust

Figure 18:
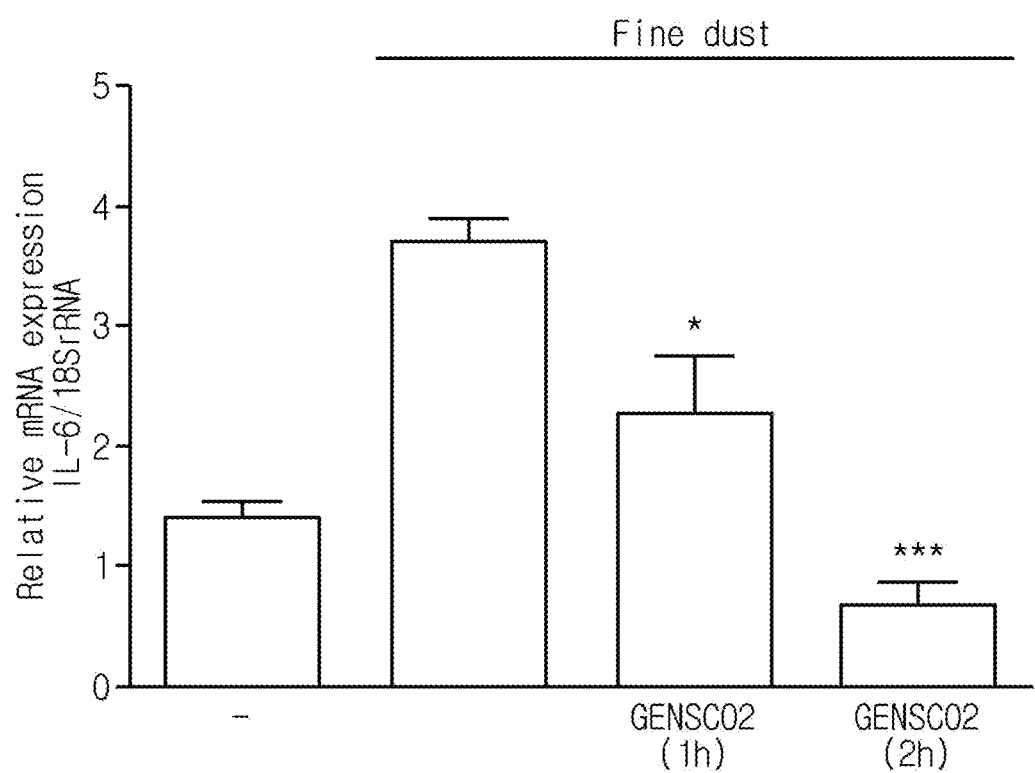
FIG. 18 is the result of confirming that the fermented filtrates of *Cutibacterium granulosum* GENSCO2 strain is effective in reduction of inflammation by fine dust.

At first, inflammation was induced by treating fine dust (Aldrich) 50 ug/ml to cells for 2 hours in which $6.5 \times 10^5$ of HaCaT human keratinocyte lines were attached in a 6-well plate, respectively, by culturing them in a 37° C. and 5% $CO_2$ incubator for 24 hours, and then it was washed out 3 times. Then, after treating the GENSCO2 fermented filtrates for 1 hour and 2 hours and then extracting RNA for each sample, the RNA expression for the inflammation response cytokine factor, IL-6, was confirmed by real-time PCR. The result was shown in FIG. 18. It was confirmed that the expression of IL-6 was significantly reduced by the GENSCO2 culture filtrates and it was further reduced in case of treatment for 2 hours.

INDUSTRIAL APPLICABILITY

The present invention provides a new *Cutibacterium granulosum* strain or culture thereof which can be used as a cosmetic composition.

The strain or culture of the present invention can be used as a cosmetic composition.

[Accession Number]

Depository institution: Korea Research Institute of Bioscience & Biotechnology

Accession number: KCTC13597BP

Deposit date: 20180724

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method of inhibiting, improving or treating acne, atopic dermatitis or inflammatory skin diseases, enhancing a skin moisturizing, or removing or reducing body odor, comprising:
administering to a subject in need thereof a therapeutically effective amount of *Cutibacterium granulosum* GENSC02 strain or its culture.

2. The method according to claim 1, wherein the *Cutibacterium granulosum* GENSC02 strain or its culture has an antibacterial activity against *Staphylococcus aureus* or *Cutibacterium acnes*.

3. The method according to claim 1, wherein the inflammatory skin diseases include an inflammatory skin disease by fine dust.

4. A method of inhibiting the growth of *Staphylococcus aureus* or *Cutibacterium acnes* of skin of a subject, comprising:
administering to the subject in need thereof a therapeutically effective amount of *Cutibacterium granulosum* GENSC02 strain (KCTC 13597BP) or its culture.

* * * * *